US007135662B2

(12) United States Patent
Shon et al.

(10) Patent No.: US 7,135,662 B2
(45) Date of Patent: Nov. 14, 2006

(54) METHOD AND APPARATUS FOR CONTROLLING MICROWAVE OVEN

(75) Inventors: Jong-Chull Shon, Suwon (KR); Won-Woo Lee, Suwon (KR); So-Hyun Lee, Suwon (KR); Keun-Seuk Oh, Suwon (KR)

(73) Assignee: Samsung Electronics Co., Ltd., Suwon-si (KR)

(*) Notice: Subject to any disclaimer, the term of this patent is extended or adjusted under 35 U.S.C. 154(b) by 232 days.

(21) Appl. No.: 10/233,561

(22) Filed: Sep. 4, 2002

(65) Prior Publication Data

US 2003/0192887 A1 Oct. 16, 2003

(30) Foreign Application Priority Data

Apr. 13, 2002 (KR) ............................... 2002-20271

(51) Int. Cl.
*H05B 6/68* (2006.01)
*G01N 33/02* (2006.01)

(52) U.S. Cl. ........................ 219/707; 219/719; 99/325; 426/241; 426/231

(58) Field of Classification Search ................ 219/716, 219/719, 702, 705, 707, 757; 73/29.01; 426/231, 426/241, 243; 99/351, 451
See application file for complete search history.

(56) References Cited

U.S. PATENT DOCUMENTS

| | | | | |
|---|---|---|---|---|
| 4,376,131 A * | 3/1983 | Mori et al. | ................. | 426/231 |
| 4,864,088 A * | 9/1989 | Hiejima et al. | ............. | 219/707 |
| 4,874,928 A * | 10/1989 | Kasai | ......................... | 219/492 |
| 5,120,916 A * | 6/1992 | Horinouchi et al. | ........ | 219/719 |
| 5,272,300 A * | 12/1993 | Edamura | .................... | 219/702 |
| 5,382,775 A * | 1/1995 | Lee | ............................ | 219/702 |
| 5,445,009 A * | 8/1995 | Yang et al. | ................ | 73/29.01 |
| 5,545,881 A * | 8/1996 | Chai et al. | .................. | 219/719 |
| 5,632,920 A | 5/1997 | Kim | | |

* cited by examiner

*Primary Examiner*—Philip H. Leung
(74) *Attorney, Agent, or Firm*—Staas & Halsey LLP

(57) ABSTRACT

A method and apparatus for controlling the operation of a microwave oven, including a magnetron generating microwaves and a sensor sensing the state of air in the cooking cavity of the oven. The cooking period is determined by searching one of two data tables in accordance with a determination result after determining whether food to be cooked is included in ascending slope-type foods or descending slope-type foods. The control method and apparatus remarkably reduces a deviation in the cooking periods by distinguishing the ascending slope-type foods from the descending slope-type foods. The control method and apparatus allows the microwave oven to appropriately cook food for a period of time which substantially matches a practically required cooking period, thus providing a good cooking result.

7 Claims, 8 Drawing Sheets

FIG. 7A

| | |
|---|---|
| T1' | T2' |
| T1'' | T2'' |
| T1''' | T2''' |
| ⋮ | ⋮ |

( T1' < T1'' < T1''' , T2' < T2'' < T2''' )

FIG. 7B

| | |
|---|---|
| T1' | T2' |
| T1'' | T2'' |
| T1''' | T2''' |
| ⋮ | ⋮ |

( T1' < T1'' < T1''' , T2''' < T2'' < T2' )

METHOD AND APPARATUS FOR CONTROLLING MICROWAVE OVEN

CROSS-REFERENCE TO RELATED APPLICATIONS

This application claims the benefit of Korean Application No. 2002-20271, filed Apr. 13, 2002, in the Korean Intellectual Property Office, the disclosure of which is incorporated herein by reference.

BACKGROUND OF THE INVENTION

1. Field of the Invention

The present invention relates, in general, to microwave ovens and, more particularly, to a method and apparatus for controlling an operation of a microwave oven during a cooking process.

2. Description of the Related Art

Microwave ovens are machines which cook food with the assistance of a variety of atmospheric sensors, such as a humidity sensor, a temperature sensor and a gas sensor, in addition to a weight sensor used for measuring the weight of food to be cooked.

The microwave oven starts a cooking process when a user operates a start button, after laying food on a turntable-type cooking tray installed in a cooking cavity of the oven and selecting a desired cooking mode in an automatic cooking menu provided on a control panel. When starting the cooking process of the microwave oven, a microprocessor receives a signal outputted from the humidity sensor, and compares the signal outputted from the humidity sensor with preset reference data stored in a data storage unit, thus calculating a target cooking period so as to control a magnetron in accordance with the calculated target cooking period.

In a conventional method of controlling the microwave oven during the cooking process, a first cooking period is determined such that the first cooking period is terminated at a time when a calculated slope of a sensor output value becomes equal to a preset reference slope. A second cooking period is determined in accordance with the first cooking period and factors preset in accordance with the kind of food to be cooked. At an end of the second cooking period, the cooking process is terminated.

FIG. 1 is a graph expressing a conventional method of controlling a cooking process for microwave ovens. As shown in FIG. 1, the total time for the cooking process of a microwave oven in the conventional method consists of an initial standby period TC, a first cooking period T1, and a second cooking period T2. Thus, when the microwave oven starts the cooking process in a selected cooking mode, a fan installed in the machine room of the oven is operated for the initial standby period TC, of about 20 minutes, at an initial stage of the cooking process, thus reducing the temperature in the cooking cavity to about a predetermined temperature. The first cooking period T1 starts at a time when the initial standby period TC ends, and is terminated at another time when a calculated slope of a sensor output value becomes equal to a preset reference slope "A". The second cooking period T2 is determined in accordance with the first cooking period T1 and factors preset in accordance with the kind of food to be cooked. In a detailed description with reference to the graph of FIG. 2, the second cooking period T2 is lengthened in proportion to a length of the first cooking period T1. That is, as the first cooking period is lengthened as shown by points T1', T1" and T1'" (where T1'<T1"<T1'"), the second cooking period T2 is proportionally lengthened, as shown by points T2', T2" and T2'" (where T2'<T2"<T2'"). Such a relation between the first and second cooking periods T1 and T2, which is expressed by a function with an ascending slope, is determined in consideration of a weight of food to be cooked. Thus, when food must be cooked having a heavy weight during one period of time, the first and second cooking periods T1 and T2 are controlled to be lengthened since such a lengthening in the first and second cooking periods T1 and T2 is desirable while cooking most kinds of foods using the microwave oven. Data for such an ascending slope-type relation between the first and second cooking periods T1 and T2 is tabulated, and stored in the data storage unit connected to a control unit of a control apparatus. During a cooking process of the microwave oven, the control unit primarily calculates a first cooking period, and secondarily searches the data table stored in the data storage unit, based on the calculated first cooking period, thus determining a second cooking period T2.

However, the conventional method of controlling a cooking process for microwave ovens is problematic in that the second cooking period T2 determined in accordance with the calculated first cooking period may not be suitable for the cooking of some kinds of foods. Thus, when cooking some kinds of foods, such as popcorn, the second cooking period T2 determined according to the calculated first cooking period is not suitable for the cooking of the food.

The cause of the problem is closely related to the kind of food or components of the food to be cooked, in addition to the position of the food in the cooking cavity and deterioration in the microwave irradiating performance of the magnetron. For example, a substantial difference between a calculated cooking period and a practically required cooking period has been experimentally shown even when a second cooking period is determined using the ascending slope-type relation between the first and second cooking periods T1 and T2 while considering the state of food and the content of moisture in the food, in the case of cooking processes of the same kind of food. Furthermore, in the case of some kinds of foods, the second cooking T2 period may be in inverse proportion to the first cooking period T1. Therefore, an improved method of determining the precise period of time for cooking in accordance with the kinds of foods to be cooked is needed.

SUMMARY OF THE INVENTION

Accordingly, a method and apparatus for controlling an operation of a microwave oven during a cooking process, which determines the precise cooking period in accordance with the kinds of foods to be cooked is provided, thus preventing poor cooking results.

Additional objects and advantages of the invention will be set forth in part in the description which follows and, in part, will be obvious from the description, or may be learned by practice of the invention.

In order to accomplish the above and other objects, the present invention provides a method of controlling a microwave oven by controlling a cooking period of the oven in accordance with an output value of a sensor sensing a state of air in a cooking cavity of the microwave oven, wherein a functional relation between a first cooking period determined in accordance with a variation in the output value of the sensor and a second cooking period determined in relation with the first cooking period has a substantially descending slope.

The method of controlling the microwave oven by controlling the cooking period of the oven in accordance with the output value of the sensor sensing the state of air in the cooking cavity of the microwave oven, comprises: selecting a kind of food to be cooked; and performing a cooking process through either of two cooking modes preset in accordance with a functional relation between a first cooking period determined in accordance with a variation in the output value of the sensor and a second cooking period determined in relation with the first cooking period, wherein the two cooking modes include a first cooking mode in which the first and second cooking periods have a proportional relation, and a second cooking mode in which the first and second cooking periods have an inverse proportional relation.

Further, the present invention provides a method of controlling the microwave oven by controlling the cooking period of the microwave oven in accordance with the output value of the sensor sensing the state of air in the cooking cavity of the microwave oven, wherein the first cooking period determined in accordance with a variation in the output value of the sensor and the second cooking period determined in relation with the first cooking period are set such that the first and second cooking periods are substantially in inverse proportion to each other.

The present invention also provides an apparatus for controlling a microwave oven having magnetron generating microwaves, and a sensor sensing a state of air in a cooking cavity of the microwave oven, the apparatus comprising: an input unit selecting a kind of food to be cooked; a storage unit storing information about a functional relation between a first cooking period determined in accordance with a variation in an output value of the sensor and a second cooking period determined in relation with the first cooking period; and a control unit determining the first and second cooking periods in accordance with a determination result after determining whether a functional relation between the first and second cooking periods corresponding to the food selected by the input unit is a relation in which the first and second cooking periods are in proportion to each other, or another relation in which the first and second cooking periods are in inverse proportion to each other, and driving the magnetron during the cooking periods, thus controlling a cooking process of the microwave oven.

BRIEF DESCRIPTION OF THE DRAWINGS

These and other objects and advantages of the present invention will become apparent and more readily appreciated from the following description of the embodiments, taken in conjunction with the accompanying drawings of which:

FIGS. 7A and 7B are data tables used in determination of second cooking periods based on first cooking periods according to the present invention, in which: FIG. 7A is a first table for ascending slope-type foods; and FIG. 7B is a second table for descending slope-type foods.

DETAILED DESCRIPTION OF THE PREFERRED EMBODIMENTS

Figure 1:
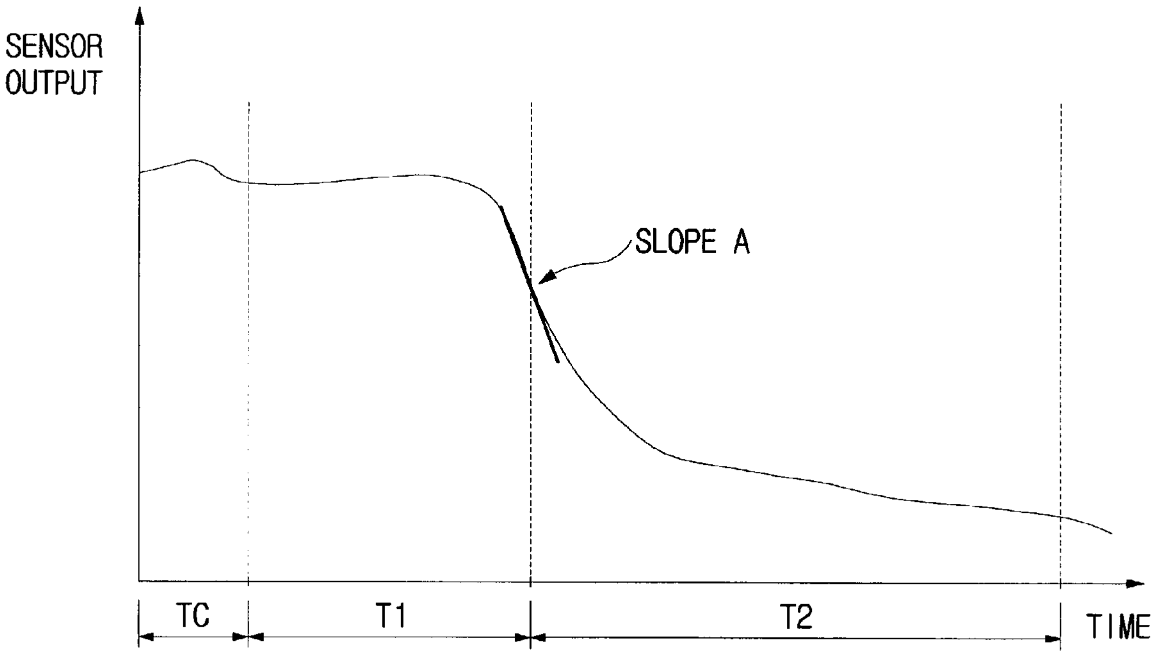
FIG. 1 is a graph expressing a conventional method of controlling an operation of a microwave oven during a cooking process.

Reference will now be made in detail to the embodiments of the present invention, examples of which are illustrated in the accompanying drawings, wherein like reference numerals refer to the like elements throughout. The embodiments are described below in order to explain the present invention by referring to the figures.

Figure 3:
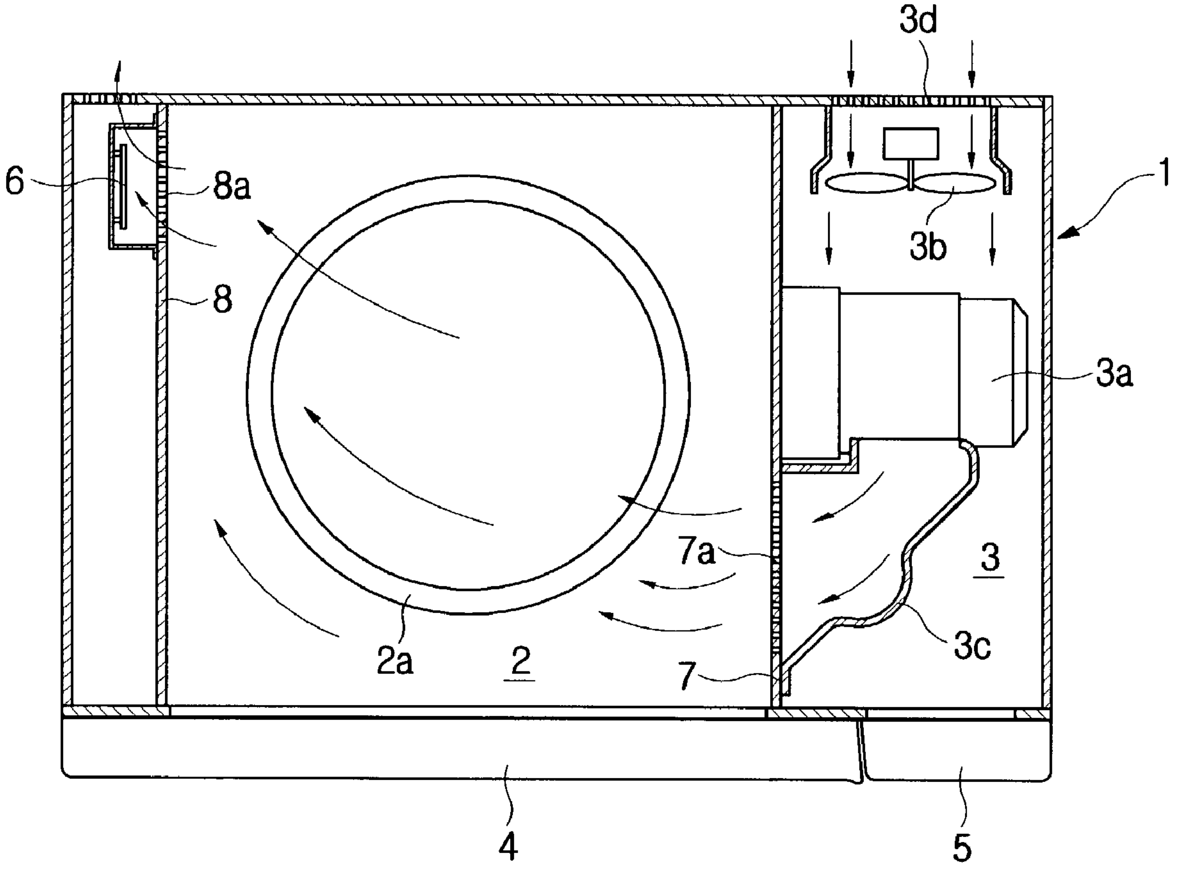
FIG. 3 is a sectional view, showing the construction of a microwave oven in accordance with an embodiment of the present invention.

FIG. 3 is a sectional view of a microwave oven in accordance with an embodiment of the present invention. As shown in FIG. 3, a microwave oven comprises a body 1, an interior of which is divided into a cooking cavity 2 and a machine room 3. A door 4 is hinged to the body 1 at a position in front of the cooking cavity 2, thus allowing a user to open or to close the cooking cavity 2. A control panel 5 is provided at the front surface of the body 1. The control panel 5 includes an input unit 5A having a plurality of control buttons, and a display unit 5B displaying information thereon during a cooking process of the microwave oven. A humidity sensor 6 is installed in the body 1 so as to sense a state of air. Thus, the moisture content of the air in the cooking cavity 2 is sensed by the humidity sensor 6.

The cooking cavity 2 is open at a front of the cooking cavity 2, and has a turntable-type cooking tray 2A on a bottom of the cooking cavity 2. An air inlet port 7A is provided at a front portion of a first sidewall 7 of the cooking cavity 2 such that the cavity 2 communicates with the machine room 3 through the air inlet port 7A. Atmospheric air is thus introduced from the machine room 3 into the cooking cavity 2 through the air inlet port 7A. An air outlet port 8A is provided at a rear portion of a second sidewall 8 of the cooking cavity 2, and discharges air from the cooking cavity 2 to outside of the body 1.

Installed in the machine room 3 are an air guide duct 3C and a variety of electric and electronic devices, for example, a magnetron 3A and a cooling fan 3B. The magnetron 3A generates microwaves, which are electromagnetic waves having very high frequencies. The cooling fan 3B sucks atmospheric air into the machine room 3 to cool the electric and electronic devices installed in the machine room 3. The air guide duct 3C guides inlet air to the air inlet port 7A. In such a case, the cooling fan 3B is installed at a position between the rear wall of the machine room 3 and the magnetron 3A. A plurality of air suction holes 3D are formed at the rear wall of the machine room 3 so as to guide atmospheric air into the machine room 3 when a suction force generated by the cooling fan 3B rotates in the machine room 3.

The humidity sensor 6 is exteriorly mounted on the second sidewall 8 of the cooking cavity 2 at a position facing the air outlet port 8A. That is, the humidity sensor 6 is installed at an air path through which the air is discharged from the cooking cavity 2 to the outside of the body 1. Therefore, the humidity sensor 6 can sense humidity of air discharged from the cooking cavity 2 to the outside through the air outlet port 8A. The humidity sensor 6 is electrically connected to a circuit board (not shown) provided in the control panel 5.

Figure 4:
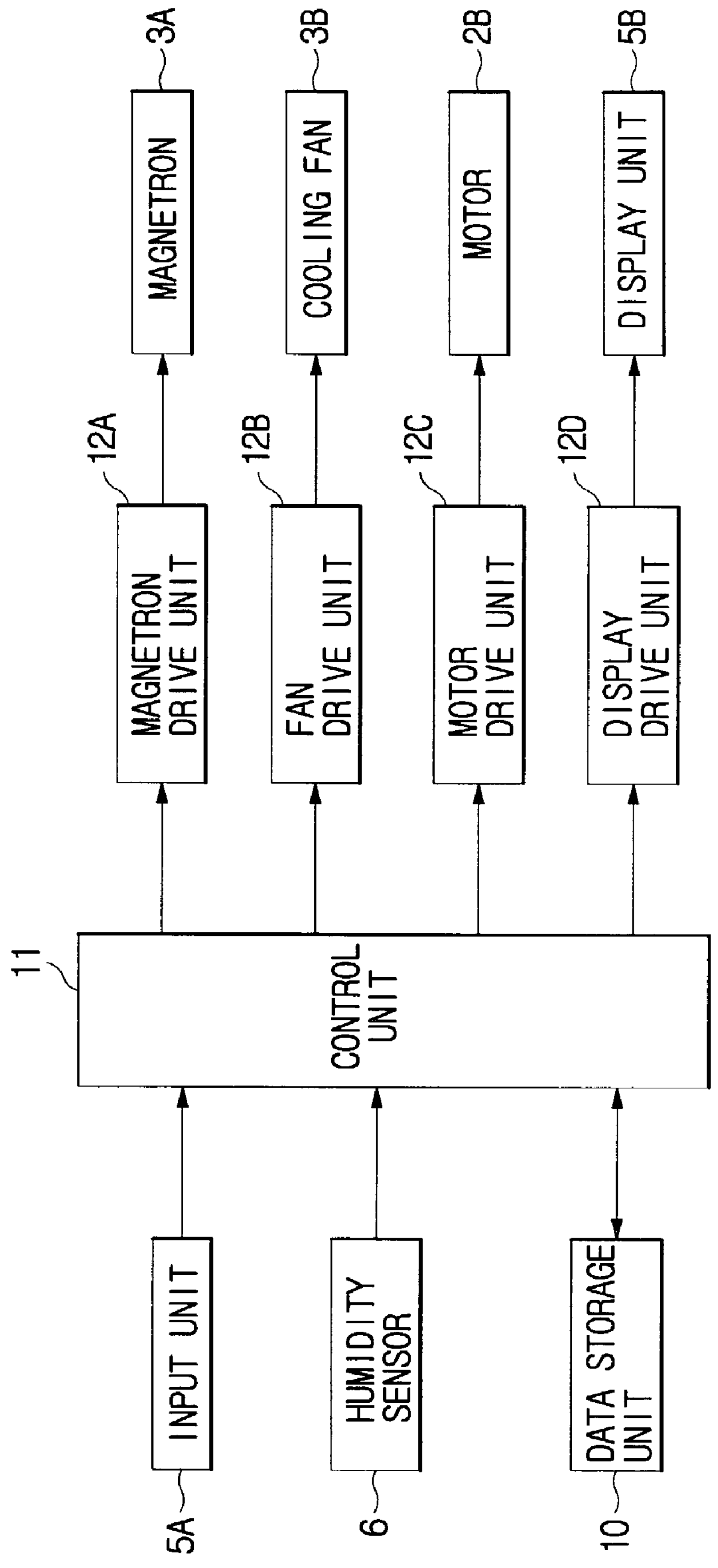
FIG. 4 is a block diagram, showing the construction of a control apparatus controlling an operation of the microwave oven in accordance with the present invention.

FIG. 4 is a block diagram, showing the construction of a control apparatus for controlling the microwave oven. As shown in FIG. 4, the control apparatus comprises a control unit 11 that controls the operation of the microwave oven. The input unit 5A provided in the control panel 5 is electrically connected to an input terminal of the control unit 11, and transmits inputted signals of the user to the control unit 11. The humidity sensor 6 and a data storage unit 10 are electrically connected to input terminals of the control unit 11. The humidity sensor 6 senses the content of moisture which is generated during a cooking process in the cooking cavity 2, laden in the air discharged from the cooking cavity 2 to the outside of the microwave oven.

The control unit 11 is electrically connected at output terminals of the control unit 11 to a plurality of drive units, such as a magnetron drive unit 12A, a fan drive unit 12B, a motor drive unit 12C, and a display drive unit 12D. The magnetron drive unit 12A, fan drive unit 12B, motor drive unit 12C, and display drive unit 12D, respectively, drive the magnetron 3A, the cooling fan 3B, a tray motor 2B, and a display unit 5B in response to control signals outputted from the control unit 11.

When the control unit 11 starts a cooking process of the microwave oven with food laid on the turntable-type cooking tray 2A in the cooking cavity 2, in response to inputted signals from the user outputted from the input unit 5A, the control unit 11 outputs a control signal to the magnetron drive unit 12A so as to drive the magnetron 3A. The magnetron 3A thus generates microwaves, and irradiates the cooking cavity 2 to cook the food on the turntable-type cooking tray 2A.

During the cooking process of the microwave oven, the cooling fan 3B sucks atmospheric air into the machine room 3, thus air-cooling the electric and electronic devices installed in the machine room 3. The inlet air in the machine room 3 also flows to the air inlet port 7A guided by the air guide duct 3C, and is introduced into the cooking cavity 2 through the air inlet port 7A. The air in the cooking cavity 2 is discharged from the cooking cavity 2 to the outside of the cooking cavity 2 through the air outlet port 8A, as shown by the arrows in FIG. 3. In such a case, moisture generated during the cooking process in the cooking cavity 2 is discharged along with air from the cooking cavity 2 to the outside of the microwave oven through the air outlet port 8A. Therefore, moisture and odor from the cooking cavity 2 can be removed to the outside during the cooking process. In such a case, the discharged air laden with moisture passes through the humidity sensor 6, so the humidity sensor 6 can sense humidity of the discharged air, and outputs a signal to the control unit 11.

Figure 2:
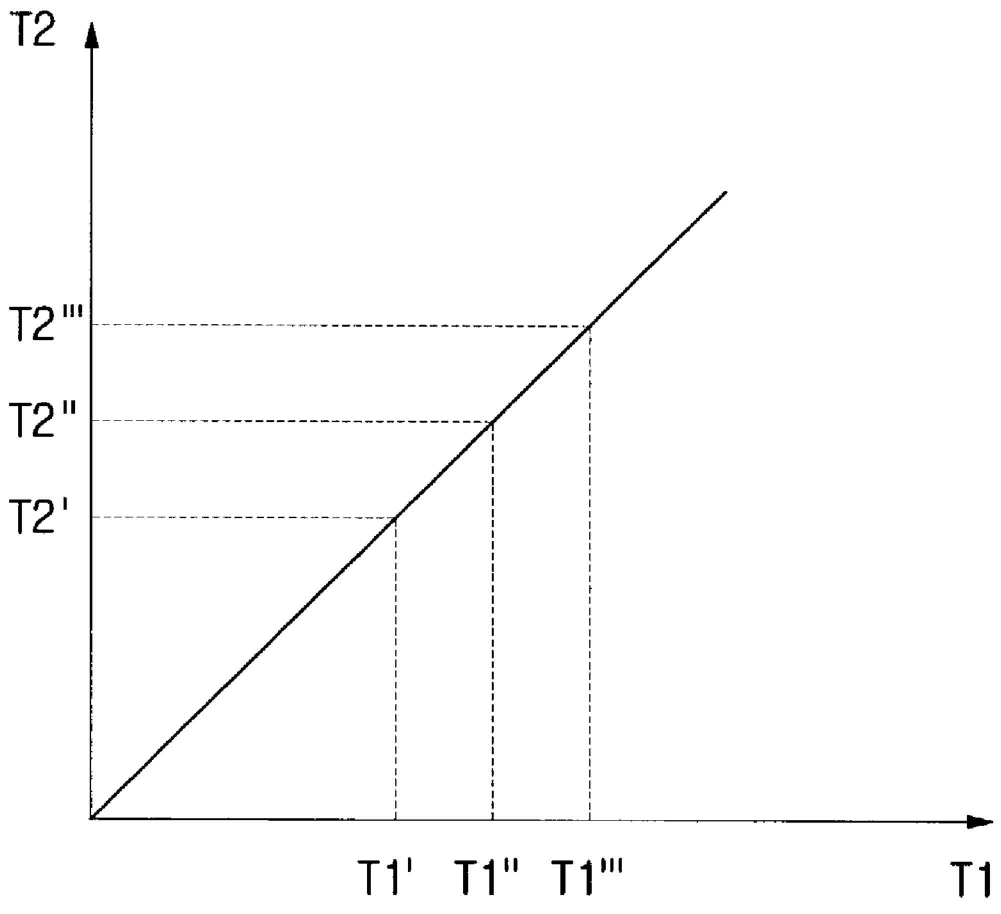
FIG. 2 is a graph expressing a concept of calculating cooking periods of a microwave oven in accordance with the conventional control method.
Figure 5:
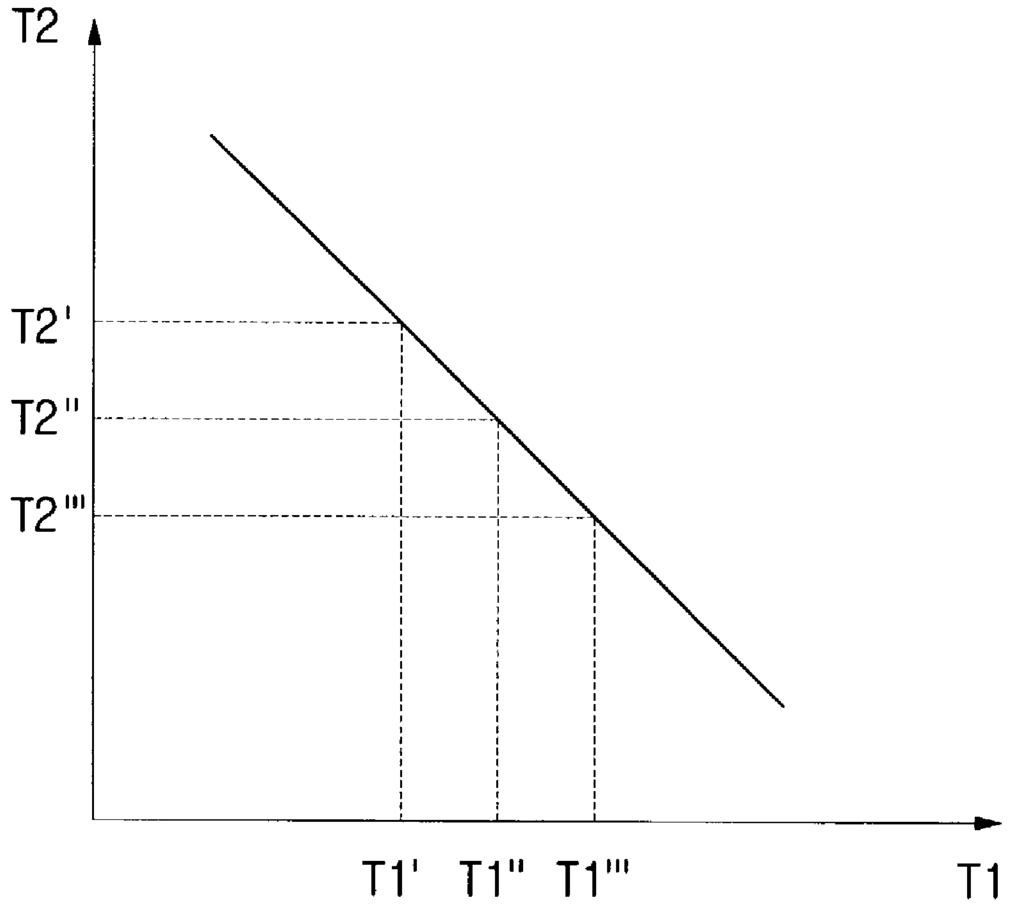
FIG. 5 is a graph expressing a concept of calculating cooking periods of the microwave oven in accordance with the present invention.

In response to the signal outputted from the humidity sensor 6, the control unit 11 performs the cooking process of the microwave oven while appropriately controlling the magnetron 3A, tray motor 2B and cooling fan 3B. In such a case, the control unit 11 determines first and second cooking periods T1 and T2 in response to the signals outputted from the humidity sensor 6. The control unit 11 determines the second cooking period T2 through either of two different methods in accordance with the kind of food to be cooked. In such a case, information about the kind of food to be cooked is obtained from a signal outputted from the input unit 5A through which a user inputs the kind of food. When the food to be cooked is included in ascending slope-type foods, the cooking process is performed through a first cooking mode. In the first cooking mode, the second cooking period T2 is determined in proportion to the first cooking period T1 in a conventional manner, as shown in the graph of FIG. 2. This means that as the first cooking period T1 is lengthened, the second cooking T2 period is lengthened proportionally. However, when the food to be cooked is included in descending slope-type foods, the cooking process is performed through a second cooking mode. In the second cooking mode, the second cooking period T2 is determined in inverse proportion to the first cooking period T1, as shown in the graph of FIG. 5. This means that as the first cooking period T1 is lengthened, the second cooking period T2 is shortened. To accomplish the above object, reference data for calculation of the second cooking periods T2 for the ascending slope-type foods is tabulated such that the second cooking periods T2', T2" and T2'" (where T2'<T2"<T2'") correspond to the first cooking periods T1', T1", T1'" (where T1'<T1"<T1'"). A first data table of FIG. 7A is thus provided. In addition, reference data for the calculation of the second cooking periods T2 for the descending slope-type foods is tabulated such that the second cooking periods T2', T2" and T2'" (where T2'>T2">T2'") correspond to the first cooking periods T1', T1", T1'" (where T1'<T1"<T1'"). A second data table of FIG. 7B is thus provided. The first and second data tables are stored in the data storage unit 10, and searched by the control unit 11 in the first and second cooking modes, respectively.

The second cooking period T2 in the first cooking mode is determined by the following expression (I), $$T2=kT1+\alpha \tag{I}$$

wherein T1 is the first cooking period, T2 is the second cooking period, k is a proportional factor, and α is a constant.

Alternatively, the second cooking period T2 in the second cooking mode is determined by the following expression (II), $$T2=-kT1+\alpha \tag{II}$$

wherein T1 is the first cooking period, T2 is the second cooking period T2, k is a proportional factor, and α is a constant.

FIG. 7B is the data table used in determination of second cooking periods based on the first cooking periods T1 when the cooking process is performed in the second cooking mode since the food is included in the descending slope-type foods. The descending slope may be variously changed in accordance with kinds of foods, so there may be several data tables used to calculate the second cooking periods in the second cooking mode. That is, even though the second cooking periods T2 determined based on the second data table for the descending slope-type foods desirably match the practically required cooking periods, the descending slopes may be different from each other in accordance with the kinds of foods. Therefore, several data tables can be provided, respectively matching the different descending slopes of foods expected to be cooked in the microwave oven.

In the case of cooking most foods of the descending slope type, the total cooking periods calculated by summing of the first and second cooking periods T2', T2" and T2'" are almost equal to each other, as shown in the graph of FIG. 5. That is, the multiplication (T1*T2) of the first cooking period T1 by the second cooking period T2 in the case of cooking the descending slope-type foods converges within a predetermined range, different from the multiplication (T1*T2) in the case of cooking the ascending slope-type foods, where a wide range of T1*T2 values is possible.

During the process of cooking some foods with low moisture content, for example, popcorn, under different cooking conditions required for different states of foods, such as frozen popcorn or normal temperature preserved popcorn, the first cooking periods T1', T1" and T1"' determined in accordance with signals outputted from the humidity sensor 6 may be different from each other, as shown in FIG. 5. However, in such a case, the second cooking periods T2', T2" and T2"' are determined in inverse proportion to the first cooking periods T1', T1" and T1"', so the total cooking periods calculated by summing the first cooking periods T1', T1" and T1"' and the second cooking periods T2', T2", and T2"' are almost equal to each other. The total cooking periods desirably match the practically required cooking periods during the cooking processes, so good cooking results are obtained.

Figure 6:
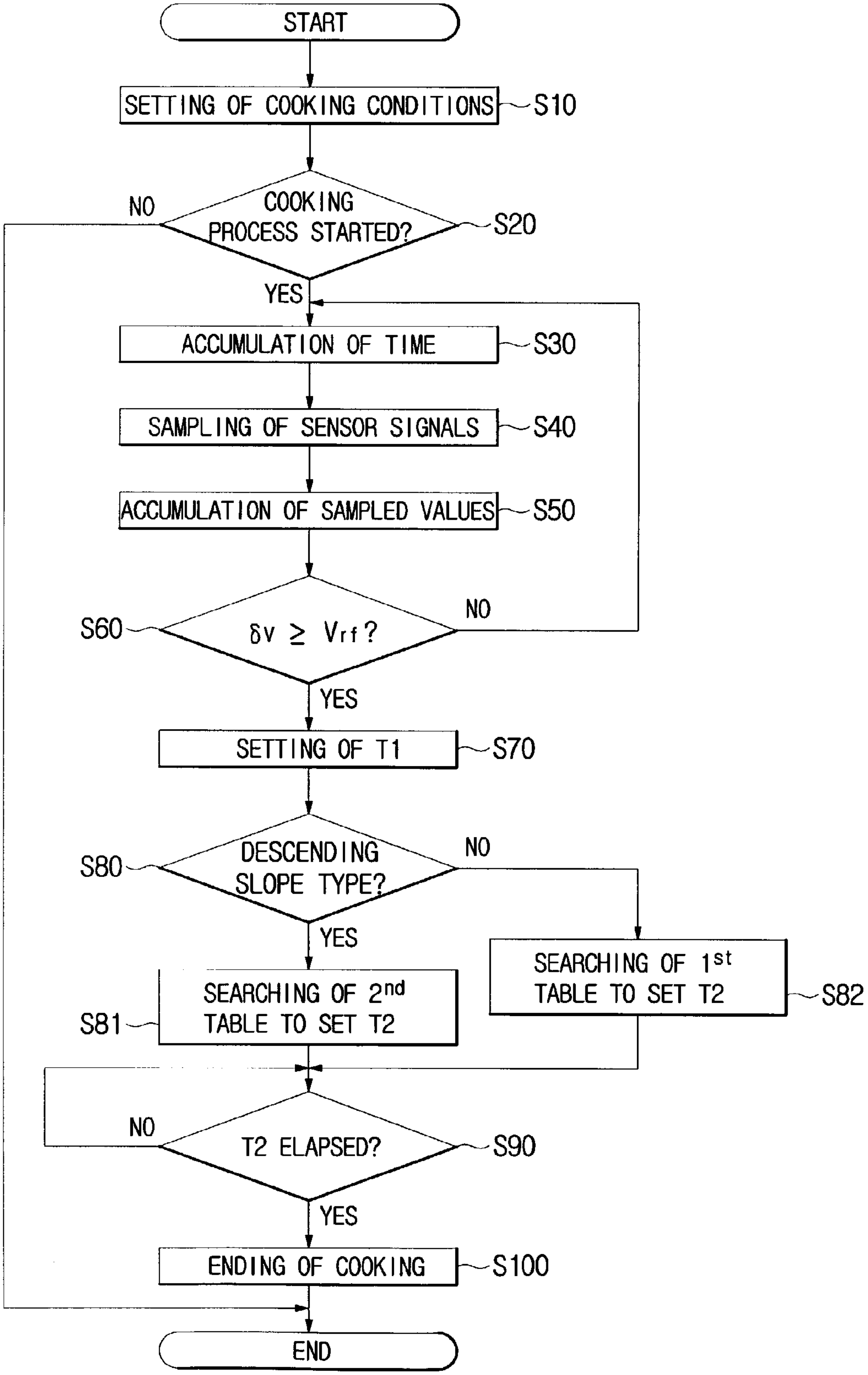
FIG. 6 is a flowchart of a method of controlling an operation of the microwave oven in accordance with the present invention.

The method of controlling the operation of the microwave oven will be described in more detail herein below with reference to FIG. 6. FIG. 6 is a flowchart of the control method according to the present invention. As shown in FIG. 6, when using the microwave oven is desired to cook food, a user lays food on the turntable-type cooking tray 2A in the cooking cavity 2. Thereafter, the user sets cooking conditions, such as the kind of food to be cooked, by manipulating the input unit 5A of the control panel 5, at S10. In such a case, the input unit 5A outputs inputted signals of the user to the control unit 11.

Upon receiving the signals outputted from the input unit 5A, the control unit 11 determines at S20 whether a cooking start signal has been inputted. When a cooking start signal is determined to be inputted, the control unit 11 outputs control signals to the magnetron drive unit 12A and the fan drive unit 12B, thus driving the magnetron 3A and the cooling fan 3B. The control unit 11 also outputs a control signal to the motor drive unit 12C, so the tray motor 2B starts to rotate the food-loaded turntable-type cooking tray 2A. During such a cooking process, the control unit 11 accumulates the cooking periods at S30.

After starting the cooking process of the microwave oven, the control unit 11 periodically samples, at S40, the signals outputted from the humidity sensor 6 for a predetermined lengthy period of time, thus calculating sampled humidity values. At S50, the control unit 11 repeatedly accumulates the periodically sampled humidity values at every sampling time, and stores the accumulated values in the data storage unit 10.

After performing such a signal sampling "n" times, the control unit 11 determines at S60 whether the difference "δV" between the present accumulated value obtained from the accumulation performed after the "nth" sampling and the previous accumulated value obtained from the accumulation performed after the "(n−1)th" sampling is greater than or equal to a preset reference value "$V_{rf}$". When the difference "δV" between the present accumulated value and the previous accumulated value is less than the preset reference value "$V_{rf}$", the procedure is returned to S30 where the control unit 11 accumulates the cooking periods. However, when the difference "δV" between the present accumulated value and the previous accumulated value is greater than or equal to the preset reference value "$V_{rf}$", the control unit 11 sets the present accumulated value to a first cooking period T1, at S70.

Thereafter, at S80, the control unit 11 determines, based on the inputted signals of the user, whether the food to be cooked is included in descending slope-type foods. When at S80 the food to be cooked is determined to be included in the descending slope-type foods, the control unit 11 searches the second data table of FIG. 7B stored in the data storage unit 10, thus determining a second cooking period T2 corresponding to the first cooking period T1, at S81. In such a case, the second cooking period T2 is in inverse proportion to the first cooking period T1, as shown in the graph of FIG. 5. Therefore, the control unit 11 determines the second cooking period T2 which is suitable to cook the descending slope-type food.

However, when at S80 the food to be cooked is determined to be not included in the descending slope-type foods, the control unit 11 determines that the food is included in the ascending slope-type foods. The control unit 11 thus searches the first data table of FIG. 7A stored in the data storage unit 10, and determines a second cooking period T2 corresponding to the first cooking period T1, at S82. In such a case, the second cooking period T2 is in proportion to the first cooking period T1, as shown in the graph of FIG. 2. Therefore, the control unit 11 determines the second cooking period T2 which matches the process of cooking the ascending slope-type food.

Thereafter, the control unit 11 determines at S90 whether the second cooking period T2 determined at S81 or S82 has elapsed or not. When the second cooking period T2 is determined to have elapsed, the control unit 11 controls the magnetron drive unit 12A, the fan drive unit 12B and the motor drive unit 12C so as to stop the magnetron 2A, the cooling fan 3B and the tray motor 2B. The cooking process thus ends at S100.

As described above, a method and apparatus for controlling the operation of a microwave oven during a cooking process is provided. In the control method and apparatus, the cooking period is determined by searching one of two data tables in accordance with a determination result after determining whether food to be cooked is included in ascending slope-type foods or descending slope-type foods. Therefore, in comparison with a conventional control method and apparatus which determines the cooking period using a single data table without distinguishing the ascending slope-type foods from descending slope-type foods, the control method and apparatus remarkably reduces a deviation in the cooking periods. The control method and apparatus of this invention is thus advantageous in that it allows the microwave oven to cook food for a time period which substantially matches a practically required cooking period, thus providing a good cooking result.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A method of controlling a microwave oven by controlling a cooking period of the microwave oven in accordance with an output value of a sensor sensing a state of air in a cooking cavity of said microwave oven, the method comprising:

selecting a kind of food to be cooked; and performing a cooking process selectively through either of two cooking modes preset in accordance with a functional relation between a first cooking period determined in accordance with a variation in the output value of the sensor and a second cooking period determined in relation with the first cooking period, wherein the two cooking modes include a first cooking mode in which the first and second cooking periods have a direct proportional relation, and a second cooking mode in which the first and second cooking periods have an inverse proportional relation to each other.

2. The method according to claim 1, wherein the second cooking period in the first cooking mode is determined by a following expression, $$T2=kT1+\alpha$$

where T1 is the first cooking period, T2 is the second cooking period, k is a proportional factor, and α is a constant.

3. The method according to claim 1, wherein the second cooking period in the second cooking mode is determined by a following expression, $$T2=-kT1+\alpha$$

where T1 is the first cooking period, T2 is the second cooking period, k is a proportional factor, and α is a constant.

4. A method of controlling a microwave oven comprising:

controlling cooking modes of the microwave oven in accordance with an output value of a sensor sensing a state of in a cooking cavity of said microwave oven, wherein a first cooking period is determined in accordance with a variation in the output value of the sensor, a second cooking period is determined in relation with the first cooking period, and wherein, in a first cooking mode, the first and the second cooking periods have a direct proportional relation, and, in a second cooking mode, the first and second cooking periods are substantially in inverse proportion to each other.

5. An apparatus for controlling a microwave oven having a magnetron generating microwaves, and a sensor sensing a state of in a cooking cavity of said microwave oven, the apparatus comprising:

an input unit selecting a kind of food to be cooked;

a storage unit storing information about a functional relation between a first cooking period determined in accordance with a variation in an output value of the sensor and a second cooking period determined in relation with the first cooking period; and a control unit determining the first and second cooking periods in accordance with a determination result after determining whether a functional relation between the first and second cooking periods corresponding to the food selected by the input unit is a relation in which the first and second cooking periods are in direct proportion to each other, or another relation in which the first and second cooking periods are in inverse proportion to each other, and driving the magnetron during the cooking periods, thus controlling a cooking process of the microwave oven.

6. A method of controlling a microwave oven comprising:

controlling cooking periods of the microwave oven in accordance with a variation in humidity of a cooking cavity of said microwave oven, wherein a first cooking period, which is determined in accordance with the variation in humidity, and a second cooking period are in an inversely proportional relation to each other, wherein the relation between said first and second cooking periods is defined by a following expression, $$T2=-kT1+\alpha$$

where T1 is the first cooking period, T2 is the second cooking period, k is a proportional factor, and α is a constant.

7. The method according to claim 6, wherein said first cooking period is a time period required to reach a predetermined humidity.

* * * * *